US012669504B2

(12) United States Patent
Miyazawa et al.

(10) Patent No.: US 12,669,504 B2
(45) Date of Patent: Jun. 30, 2026

(54) METHOD FOR DETECTING PARTICULATE SUBSTANCE BY IMMUNOCHROMATOGRAPHY, AND KIT FOR THE SAME

(71) Applicants: DAI NIPPON TORYO CO., LTD., Osaka (JP); SHIMADZU CORPORATION, Kyoto (JP)

(72) Inventors: Yuta Miyazawa, Utsunomiya (JP); Hirotaka Fujimoto, Kyoto (JP); Makoto Watanabe, Kyoto (JP); Taka-Aki Sato, Kyoto (JP)

(73) Assignees: DAI NIPPON TORYO CO., LTD., Osaka (JP); SHIMADZU CORPORATION, Kyoto (JP)

( * ) Notice: Subject to any disclaimer, the term of this patent is extended or adjusted under 35 U.S.C. 154(b) by 603 days.

(21) Appl. No.: 18/265,816

(22) PCT Filed: Dec. 7, 2021

(86) PCT No.: PCT/JP2021/044842
§ 371 (c)(1),
(2) Date: Jun. 28, 2023

(87) PCT Pub. No.: WO2022/124288
PCT Pub. Date: Jun. 16, 2022

(65) Prior Publication Data

US 2024/0060980 A1 Feb. 22, 2024

(30) Foreign Application Priority Data

Dec. 7, 2020 (JP) ................................. 2020-202418

(51) Int. Cl.
*B01L 3/00* (2006.01)
*B01D 15/08* (2006.01)
(Continued)

(52) U.S. Cl.
CPC . *G01N 33/57515* (2026.01); *G01N 33/54387* (2021.08); *G01N 33/57585* (2026.01); *G01N 2470/04* (2021.08)

(58) Field of Classification Search
CPC ....... G01N 33/57515; G01N 33/54387; G01N 33/57585; G01N 2470/04; G01N 33/92; G01N 33/54393
See application file for complete search history.

(56) References Cited

U.S. PATENT DOCUMENTS

| | | | |
|---|---|---|---|
| 2014/0087395 A1 | 3/2014 | Takeuchi et al. | |
| 2015/0168400 A1 | 6/2015 | Ichiki et al. | |

(Continued)

FOREIGN PATENT DOCUMENTS

| | | |
|---|---|---|
| JP | 2008-058334 A | 3/2008 |
| JP | 4622054 B2 | 2/2011 |

(Continued)

OTHER PUBLICATIONS

Japan Patent Office, "Office Action for Japanese Patent Application 2020-202418," Aug. 24, 2023.

(Continued)

*Primary Examiner* — Jennifer Wecker
*Assistant Examiner* — Oyeleye Alexander Alabi
(74) *Attorney, Agent, or Firm* — HAUPTMAN HAM, LLP

(57) ABSTRACT

An object of the present invention is to provide a method for detecting particulate substances with a high degree of sensitivity, while suppressing the generation of non-specific signals. According to the present invention, the generation of non-specific signals in the background can be suppressed by blocking a membrane of a test strip which is used for immunochromatography with a blocking composition
(Continued)

including a polymer-based blocking agent having, in its side chain, a substituent represented by the following formula:

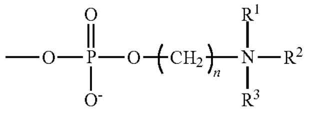

(wherein $R^1$, $R^2$, and $R^3$ are each independently a hydrogen atom, a $C_{1-6}$ alkyl group, or a $C_{1-6}$ hydroxyalkyl group; and n is an integer of 1 to 4), and having a weight average molecular weight (Mw) of $1\times10^3$ to $1\times10^7$.

10 Claims, 7 Drawing Sheets

(51) Int. Cl.

| | |
|---|---|
| ***B01F 33/302*** | (2022.01) |
| ***B01F 33/3033*** | (2022.01) |
| ***B01J 8/00*** | (2006.01) |
| ***B01J 8/02*** | (2006.01) |
| ***B01J 20/285*** | (2006.01) |
| ***B01J 20/287*** | (2006.01) |
| ***B01J 20/32*** | (2006.01) |
| ***B01L 7/00*** | (2006.01) |
| ***B01L 9/00*** | (2006.01) |
| ***B65G 47/80*** | (2006.01) |
| ***B82Y 20/00*** | (2011.01) |
| ***B82Y 30/00*** | (2011.01) |
| ***B82Y 40/00*** | (2011.01) |
| ***C08L 5/08*** | (2006.01) |
| ***C12M 1/34*** | (2006.01) |
| ***C12M 3/06*** | (2006.01) |
| ***C12N 1/14*** | (2026.01) |
| ***C12N 1/20*** | (2026.01) |
| ***C12Q 1/02*** | (2006.01) |
| ***C12Q 1/6806*** | (2018.01) |
| ***C12Q 1/6844*** | (2018.01) |
| ***C12Q 1/6848*** | (2018.01) |
| ***C12Q 1/6851*** | (2018.01) |
| ***C12Q 1/686*** | (2018.01) |
| ***G01K 1/14*** | (2021.01) |
| ***G01N 1/44*** | (2006.01) |
| ***G01N 15/10*** | (2024.01) |
| ***G01N 15/14*** | (2024.01) |
| ***G01N 15/1433*** | (2024.01) |
| ***G01N 21/01*** | (2006.01) |
| ***G01N 21/03*** | (2006.01) |
| ***G01N 21/05*** | (2006.01) |
| ***G01N 21/29*** | (2006.01) |
| ***G01N 21/33*** | (2006.01) |
| ***G01N 21/35*** | (2014.01) |
| ***G01N 21/65*** | (2006.01) |
| ***G01N 21/75*** | (2006.01) |
| ***G01N 21/77*** | (2006.01) |
| ***G01N 27/07*** | (2006.01) |
| ***G01N 27/28*** | (2006.01) |
| ***G01N 27/416*** | (2006.01) |
| ***G01N 30/02*** | (2006.01) |
| ***G01N 30/60*** | (2006.01) |
| ***G01N 30/72*** | (2006.01) |
| ***G01N 31/10*** | (2006.01) |
| ***G01N 31/12*** | (2006.01) |
| ***G01N 33/543*** | (2006.01) |
| ***G01N 33/557*** | (2006.01) |
| ***G01N 33/564*** | (2006.01) |
| ***G01N 33/574*** | (2006.01) |
| ***G01N 33/575*** | (2026.01) |
| ***G01N 33/57515*** | (2026.01) |
| ***G01N 33/58*** | (2006.01) |
| ***G01N 33/68*** | (2006.01) |
| ***G01N 35/00*** | (2006.01) |
| ***H05B 45/10*** | (2020.01) |

(56) References Cited

U.S. PATENT DOCUMENTS

| | | | | |
|---|---|---|---|---|
| 2016/0202251 | A1 | 7/2016 | Goh et al. | |
| 2019/0204308 | A1 | 7/2019 | Busseret et al. | |
| 2020/0025750 | A1 | 1/2020 | Shiba et al. | |
| 2020/0191778 | A1* | 6/2020 | Huang | G01N 33/588 |
| 2022/0011306 | A1* | 1/2022 | Kohno | G01N 33/553 |

FOREIGN PATENT DOCUMENTS

| | | | |
|---|---|---|---|
| JP | 2013-053897 | A | 3/2013 |
| JP | 2015-230280 | A | 12/2015 |
| JP | 2017-106915 | A | 6/2017 |
| JP | 6248603 | B2 | 12/2017 |
| JP | 2018-077171 | A | 5/2018 |
| JP | 2019-007984 | A | 1/2019 |
| JP | 2019-163068 | A | 9/2019 |
| WO | 2014/030590 | A1 | 2/2014 |
| WO | 2016/017037 | A1 | 2/2016 |
| WO | 2017/204187 | A1 | 11/2017 |

OTHER PUBLICATIONS

Yu, Qiang et al., "Development of a lateral flow aptamer assay strip for facile identification of theranostic exosomes isolated from human lung carcinoma cells," Analytical Biochemistry, Jan. 20, 2020, vol. 594, No. 113591.
Oliveira-Rodriguez, M. et al., "Point-of-care detection of extracellular vesicles: Sensitivity optimization and multiple-target detection," Biosensors and Bioelectronics, Aug. 2, 2016, vol. 87, pp. 38-45.
PCT/ISA/210, "International Search Report for PCT International Application No. PCT/JP2021/044842," Feb. 1, 2022.
EP Extended Search Report dated May 23, 2024 for EP Patent Application No. 21903387.5, 7 pp.
"Extracellular Vesicles: Current Analytical Techniques for Detection and Quantification", Esther Serrano-Pertierra et al., Biomolecules, vol. 10, No. 6, May 28, 2020, p. 824, 19 pp.

* cited by examiner

METHOD FOR DETECTING PARTICULATE SUBSTANCE BY IMMUNOCHROMATOGRAPHY, AND KIT FOR THE SAME

RELATED APPLICATIONS

The present application is National Phase of International Application No. PCT/JP2021/044842 filed Dec. 7, 2021, and claims priority from Japanese Application No. 2020-202418, filed Dec. 7, 2020, the disclosure of which is hereby incorporated by reference herein in its entirety.

TECHNICAL FIELD

The present invention relates to a method for detecting a particulate substance by immunochromatography, and a kit for the same.

BACKGROUND TECHNOLOGY

Particulate substances such as extracellular vesicles and viruses can be detected by immunochromatography (Patent Documents 1 and 2, as well as Non-Patent Documents 1 and 2). Immunochromatography is a test method that enables more rapid detection compared with Western blotting and ELISA. This method is superior to measurements by NanoSight or the like in terms of, for example, capability of detecting target particulate substances without isolation, and capability of detecting particulate substances comprising specific non-detectable substances on their surfaces separately from other particulate substances. Further, exosomes which are extracellular vesicles are particulate substances that are contained in various body fluids, such as breast milk, saliva, and tears, as well as blood and urine. Since exosomes are known to contain microRNA specific to cells, they have been attracting attention as target substances in cancer diagnosis using body fluids.

As the sensitivity of inspection increases, it is not only useful for early detection and prevention of diseases, but also able to reduce the amount of samples required for testing, thus reducing the burden on the subjects. Patent Documents 3 and 4 indicate that polymer-based blocking agents having a phosphorylcholine group or the like can suppress non-specific adsorption or accelerate biochemical reactions.

However, Patent Documents 3 and 4 do not indicate that the polymer-based blocking agents are used for immunochromatography or for the detection of particulate substances.

Citation List

Patent Documents

Patent Document 1: JP2015-230280A

Patent Document 2: Japanese Patent Application No. 2019-163068

Patent Document 3: JP6248603B

Patent Document 4: JP4622054B

SUMMARY OF THE INVENTION

Technical Problem

Particulate substances comprising a plurality of antigens on their surfaces are more likely to generate non-specific signals because they have a larger contact surface than simple proteins. In particular, when an attempt is made to detect such particulate substances by immunochromatography with high intensity, non-specific signals in the background are also increased, which rather reduces the sensitivity at the detection site. Accordingly, an object of the present invention is to provide a method for detecting particulate substances with high sensitivity while suppressing the generation of non-specific signals.

Solution to Problem

As a result of extensive studies to achieve the above object, the present inventors found that a specific blocking agent is effective to suppress non-specific signals in the background in the detection of particulate substances, particularly detection by immunochromatography. Thus, the present invention has been completed. Specifically, the present invention provides a method for detecting a particulate substance by immunochromatography, a method for producing a kit for the same, and a kit for the same as described below.

[1] A method for detecting a particulate substance by immunochromatography, the particulate substance comprising, on its surface, a plurality of substances to be bound including a first substance to be bound and a second substance to be bound that may be the same or different from each other, the method comprising steps of:

providing a test strip comprising a membrane on which first specific binding substance for the first substance to be bound is immobilized;

providing a second specific binding substance for the second substance to be bound, the second specific binding substance binding to a labeling substance;

contacting a sample containing the particulate substance with the first specific binding substance to capture the particulate substance on the membrane;

contacting the particulate substance with the second specific binding substance to label the particulate substance; and detecting the labeled particulate substance captured on the membrane;

wherein the membrane is blocked with a blocking composition comprising a polymer-based blocking agent having, in its side chain, a substituent represented by the following formula:

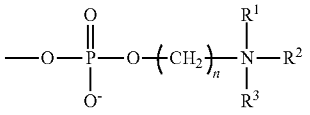

(wherein $R^1$, $R^2$, and $R^3$ are each independently a hydrogen atom, a $C_{1-6}$ alkyl group, or a $C_{1-6}$ hydroxyalkyl group; and n is an integer of 1 to 4), and having a weight average molecular weight (Mw) of $1\times10^3$ to $1\times10^7$.

[2] The method according to the above [1], wherein the particulate substance comprises extracellular vesicles.

[3] The method according to the above [2], wherein the extracellular vesicles are exosomes.

[4] The method according to any one of the above [1] to [3], wherein the detecting step is performed by measuring chemiluminescence or fluorescence.

[5] The method according to any one of the above [1] to [4], wherein the labeling step is performed in the presence of the polymer-based blocking agent.

[6] The method according to any one of the above [1] to [5], wherein the polymer-based blocking agent is LIPIDURE®.

[7] The method according to any one of the above [1] to [6], wherein the blocking composition further comprises an additional blocking agent.

[8] A method for producing a kit for detecting a particulate substance by immunochromatography, the particulate substance comprising, on its surface, a plurality of substances to be bound including a first substance to be bound and a second substance to be bound that may be the same or different from each other, the method comprising steps of:

providing a test strip comprising a membrane on which first specific binding substance for the first substance to be bound is immobilized; and providing, in order to block the membrane, a blocking composition comprising a polymer-based blocking agent having, in its side chain, a substituent represented by the following formula:

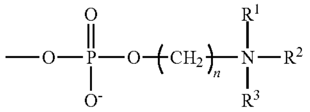

(wherein $R^1$, $R^2$, and $R^3$ are each independently a hydrogen atom, a $C_{1-6}$ alkyl group, or a $C_{1-6}$ hydroxyalkyl group; and n is an integer of 1 to 4), and having a weight average molecular weight (Mw) of $1\times10^3$ to $1\times10^7$.

[9] The production method according to the above [8], further comprising a step of blocking the membrane with the blocking composition.

[10] The production method according to the above [8] or [9], further comprising steps of:

providing a second specific binding substance for the second substance to be bound, the second specific binding substance binding to a labeling substance; and blocking the second specific binding substance with the blocking composition.

[11] A kit for detecting a particulate substance by immunochromatography, the particulate substance comprising, on its surface, a plurality of substances to be bound including a first substance to be bound and a second substance to be bound that may be the same or different from each other, the kit comprising:

a test strip comprising a membrane on which a first specific binding substance for the first substance to be bound is immobilized; and a second specific binding substance for the second substance to be bound, the second specific binding substance binding to a labeling substance;

wherein in order to block the membrane, the kit further comprises a blocking composition comprising a polymer-based blocking agent having, in its side chain, a substituent represented by the following formula:

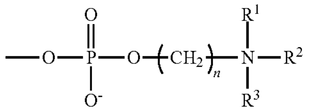

(wherein $R^1$, $R^2$, and $R^3$ are each independently a hydrogen atom, a $C_{1-6}$ alkyl group, or a $C_{1-6}$ hydroxyalkyl group; and n is an integer of 1 to 4), and having weight average molecular weight (Mw) of $1\times10^3$ to $1\times10^7$; or the membrane is blocked with the blocking composition.

Advantageous Effects of Invention

According to the present invention, the generation of non-specific signals in the background can be suppressed by blocking a membrane of a test strip which is used for immunochromatography with a blocking composition comprising a specific polymer-based blocking agent. Therefore, it allows detection of particulate substances with high sensitivity by immunochromatography.

DESCRIPTION OF EMBODIMENTS

Figure 1:
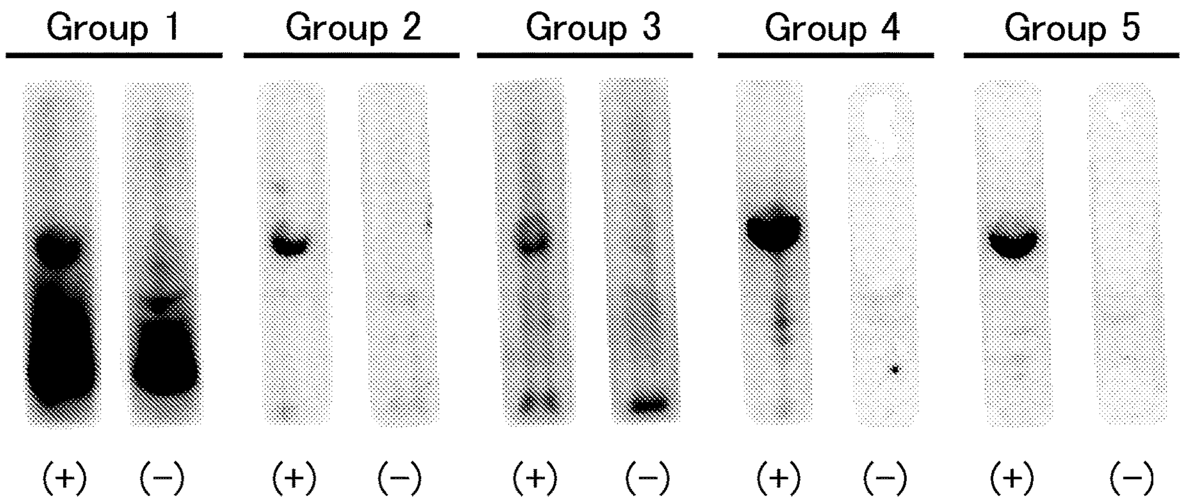
FIG. 1 shows photographs of membranes after luminescence on which an exosome-containing test liquid (+) or an exosome-free reference liquid (−) was developed.

The present invention is described in more detail below.

The present invention relates to a method for detecting particulate substances by immunochromatography. "Immunochromatography" described in the present specification is a method for detecting a target substance in a sample using a substance that specifically binds to the target substance, and refers to not only a lateral flow detection method that separates the target substance by moving the sample on the membrane, but also a flow-through (vertical flow) detection method that separates the target substance by moving the sample vertically with respect to the membrane. The "particulate substance" described in the present specification refers to a particulate substance having a size that can be detected by immunochromatography. The particulate substance comprises, on its surface, a plurality of at least one kind of substance to be bound. The substances to be bound include a first substance to be bound and a second substance to be bound that may be the same or different from each other. The particle size of the particulate substance is not particularly limited, and may be, for example, about 10 μm or less, or in an embodiment, it may be about 5 μm or less, about 1 μm or less, about 500 nm or less, or about 200 nm or less. Specifically, the particulate substance may be, for example, extracellular vesicles such as exosomes, microvesicles, apoptotic bodies, and large oncosomes; viruses such as rhinovirus, coronavirus, influenza virus, parainfluenza virus, adenovirus, RS virus, enterovirus, rotavirus, human papillomavirus, human immunodeficiency virus, hepatitis B virus, Zika virus, and dengue virus; or bacteria such as *Chlamydia*, *Treponema pallidum*, hemolytic *Streptococcus*, anthrax, *Staphylococcus aureus*, *Escherichia coli*, *Salmonella*, *Salmonella typhimurium*, *Salmonella paratyphi*, *Pseudomonas aeruginosa*, and *Vibrio parahaemolyticus*.

As the sample containing the particulate substance, any sample can be used without particular limitation as long as it can be subjected to immunochromatography. As the sample to be applied to the detection method of the present invention, a sample collected from, a living body or a culture medium may be used as is, or a sample that is purified, partially purified, or concentrated by pretreatment, such as filtration or centrifugation, may be used. Specific examples of the sample include body fluids such as blood (whole blood, serum, or plasma), cerebral spinal fluid, tears, breast milk, alveolar lavage fluid, malignant pleural effusion, synovial fluid, urine, amniotic fluid, ascites, semen, saliva, and lymph; preservative solutions for tissue sections, cell culture supernatants, and the like.

The detection method of the present invention comprises steps of:

- providing a test strip comprising a membrane on which a first specific binding substance for the first substance to be bound is immobilized;
- providing a second specific binding substance for the second substance to be bound, the second specific binding substance binding to a labeling substance;
- contacting a sample containing the particulate substance with the first specific binding substance to capture the particulate substance on the membrane;
- contacting the particulate substance with the second specific binding substance to label the particulate substance; and
- detecting the labeled particulate substance captured on the membrane;
- wherein the membrane is blocked with a blocking composition comprising a specific polymer-based blocking agent.

The polymer-based blocking agent used in the detection method of the present invention is, among blocking agents used to suppress non-specific signals in so-called immunochemical measurement methods, particularly an artificially synthesized polymer and has, in its side chain, a substituent represented by the following formula:

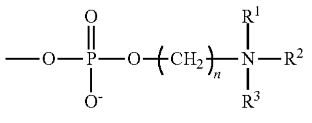

(wherein $R^1$, $R^2$, and $R^3$ are each independently a hydrogen atom, a $C_{1-6}$ alkyl group, or a $C_{1-6}$ hydroxyalkyl group; and n is an integer of 1 to 4), preferably a phosphorylcholine group, and has a weight average molecular weight (Mw) of about $1\times10^3$ to about $1\times10^7$, preferably about $5\times10^3$ to about $1\times10^6$. In an embodiment, the polymer-based blocking agent may have at least one additional side chain selected from the group consisting of a cationic side chain, an anionic side chain, a hydrogen-bonding side chain, and a hydrophobic side chain. The polymer-based blocking agent is not particularly limited. For example, LIPIDURE®, preferably Polymer LIPIDURE®-BL series blocking agents (produced by NOF Corporation), may be used. In a specific situation in which the particulate substance is detected by immunochromatography, the polymer-based blocking agent can effectively suppress the generation of non-specific signals in the background.

The method for measuring the weight average molecular weight of the polymer-based blocking agent is not particularly limited. For example, the weight average molecular weight can be measured by gel permeation chromatography (GPC) and using a mass spectrometer such as matrix-assisted laser desorption/ionization time-of-flight mass spectrometer (MALDI-TOFMS). More specifically, a 0.1 M sodium nitrate aqueous solution is used for dilution so that the amount of the polymer-based blocking agent is 0.5% by weight, followed by filtration with a 0.45-μm cellulose acetate cartridge filter, after which the weight average molecular weight can be measured by GPC under the following conditions.

Device: HLC-8320GPC (produced by Tosoh Corporation)

Column: TSK gel guard column PWXL (6.0 mm I.D.×4 cm)+TSK gel GMPWXL (7.8 mm a I.D.×30 cm)×2 (produced by Tosoh Corporation)

Mobile phase: 0.1 M sodium nitrate aqueous solution

Standard substance: standard PEO/PEG (produced by Agilent Technologies)

Detection condition: RI detector polarity (+)

Flow rate: 1.0 mL/min

Column temperature: 40° C.

Sample solution injection amount: 100 μL

Measurement time: 25 minutes

In an embodiment, the blocking composition further comprises an additional blocking agent. As the additional blocking agent, any blocking agent generally used in the art can be adopted without particular limitation. For example, the additional blocking agent may be bovine serum albumin (BSA), skim milk, casein, a commercially available blocking reagent, or the like. Use of such additional blocking agent in combination with the polymer-based blocking agent can further suppress the generation of non-specific signals in the background.

In the particulate substance targeted by the detection method of the present invention, when the first substance to be bound and the second substance to be bound are the same, the binding site of the first specific binding substance in the first substance to be bound may be the same as or different from the binding site of the second specific binding substance in the second substance to be bound. Even when both binding sites are the same, the particulate substance has a plurality of substances to be bound on its surface, which allows labeling with the second specific binding substance even after it is captured by the first specific binding substance.

The first specific binding substance is immobilized on the membrane, and can capture the particulate substance having the first substance to be bound on the membrane. As the membrane, any membrane used as an immunochromatographic test strip (immunochromatographic test paper) (i.e., a membrane that has the ability to immobilize the first specific binding substance, and that does not prevent the liquid from passing in the desired direction) can be used without particular limitations. For example, the membrane may be a porous membrane having capillarity and capable of transporting a liquid and components dispersed therein by absorption. The material of the membrane is not particularly limited, and may be, for example, cellulose, nitrocellulose, cellulose acetate, polyvinylidene fluoride (PVDF), glass fiber, nylon, polyketone, or the like.

As the first specific binding substance, any substance can be adopted without particular limitation as long as it can be immobilized on the membrane and can capture the particulate substance to be detected on the membrane through the formation of a complex with the first substance to be bound. Specific examples of combinations of the first substance to be bound and the first specific binding substance include an antigen and an antibody that binds thereto, an antibody and an antigen that binds thereto, a sugar chain or complex carbohydrate and a lectin that binds thereto, a lectin and a sugar chain or complex carbohydrate that binds thereto, a hormone or cytokine and a receptor that binds thereto, a receptor and a hormone or cytokine that binds thereto, a protein and a nucleic acid aptamer or peptide aptamer that binds thereto, an enzyme and a substrate that binds thereto, a substrate and an enzyme that binds thereto, biotin and avidin or streptavidin, avidin or streptavidin and biotin, IgG and protein A or protein G, protein A or protein G and IgG, T-cell immunoglobulin and mucin domain-containing molecule 4 (Tim 4) and phosphatidylserine (PS), PS and Tim 4, a first nucleic acid and a second nucleic acid that binds (hybridizes) thereto, and the like. The second nucleic acid may be a nucleic acid containing a sequence complementary to the first nucleic acid.

When the first substance to be bound is an antigen, the first specific binding substance may be an antibody. Specifically, when the particulate substance is an exosome, the first substance to be bound may be CD9, CD63, or CD81, and the first specific binding substance may be anti-CD9 antibody, anti-CD63 antibody, or anti-CD81 antibody. The antibody may be a polyclonal antibody, a monoclonal antibody, a single-chain antibody, or a fragment thereof, all of which specifically bind to the antigen. The fragment may be an F(ab) fragment, an F(ab') fragment, an $F(ab')_2$ fragment, or an F(v) fragment.

The second specific binding substance binds to a labeling substance, and can label the particulate substance having the second substance to be bound. The second specific binding substance and the labeling substance may be combined to form a complex, regardless of the mode of binding, such as covalent or non-covalent binding or direct or indirect binding. As the second specific binding substance, any substance can be adopted without particular limitation as long as the particulate substance to be detected can be detected by the formation of a complex with the second substance to be bound. Specific examples of combinations of the second substance to be bound and the second specific binding substance include the same as the specific examples of combinations of the first substance to be bound and the first specific binding substance described above.

The "labeling substance" described in the present specification refers to a substance that provides a marker for detecting the binding between the second specific binding substance and the second substance to be bound. The labeling substance is not particularly limited, and may be, for example, a chemiluminescence substance, a fluorescence substance, metal nanoparticies, or the like. The "chemiluminescence substance" described in the present specification refers to a substance involved in the chemical reaction that produces photons. Examples thereof include chemiluminescence enzyme that catalyzes the chemical reaction. The chemiluminescence enzyme is not particularly limited, and may be, for example, peroxidases such as horseradish peroxidase (SEP), alkaline phosphatase, or luciferase. The peroxidases catalyze the reaction of luminol-based compounds, the alkaline phosphatase catalyzes the reaction of dioxetane-based compounds, and the luciferase catalyzes the reaction of luciferin-based compounds.

The "fluorescence substance" described in the present specification refers to a substance that absorbs excitation light and emits fluorescence. The fluorescence substance is not particularly limited, and may be, for example, fluorescein isothiocyanate (FITC), phycoerythrin (PE), allophycocyanin (APC), or a derivative thereof.

The "metal nanoparticies" described in the present specification refer to particles made of metal and having a size on the order of nanometers (nm). The metal is not particularly limited, and may be gold or silver. The metal nanoparticles are not particularly limited, and may be anisotropic metal nanoparticles or spherical metal nanoparticles.

As the method for bonding the second specific binding substance and the labeling substance, general bonding methods can be used without particular limitation. Applicable examples include methods for directly bonding the labeling substance and the second specific binding substance using physical adsorption, chemical adsorption (covalent bonding to the surface), chemical bonding (covalent bonding, coordination bonding, ionic bonding, or metal bonding), or the like; and methods for directly or indirectly bonding the second specific binding substance to the terminal, main chain or side chain of a water-soluble polymer bonded to the surface of the labeling substance.

In the detecting step of the present invention, the labeling substance aggregated at the detection site can be detected visually or using a detection device, either directly or by causing a chemical reaction or irradiation with excitation light. The detection device is not particularly limited. For example, a mass spectrometer, an immunochromatographic reader, or an image analyzer including a CCD imager, a scanner, image processing software, etc. may be used. In an embodiment, the detection step is performed by measuring chemiluminescence or fluorescence. Specifically, when the labeling substance is HRP, a substrate solution containing luminal, hydrogen peroxide, an enhancer, and the like is added dropwise on immunochromatographic test paper after immunochromatographic test, and the resulting luminescence can be detected by an X-ray film or a CCD imager. In the case of such chemiluminescence detection, photons produced as a result of the reaction between the enzyme and the substrate, rather than the amount of enzyme present, are detected as signals. Accordingly, the amplification of reaction products by increasing the reaction time and detection time enables detection with high sensitivity.

In an embodiment, the detecting step may include a step of quantifying the particulate substance. For example, for a standard sample whose content of the particulate substance has been clarified by measurement with a NanoSight nanoparticle analysis system or the like, a calibration curve may be created based on the luminance difference determined with scanner, image processing software, etc., or the absorbance measured with an immunochromatographic reader, and the content of the particulate substance in an unknown sample may be determined.

In the detection method of the present invention, the order of the capturing step and the labeling step is not particularly limited. That is, the particulate substance may be labeled after the particulate substance is captured on the membrane, or the particulate substance may be captured on the membrane after the particulate substance is labeled.

In an embodiment, the labeling step is performed in the presence of the polymer-based blocking agent. When labeling is performed under such condition, non-specific adsorption of the second specific binding substance can be suppressed.

In another embodiment, the present invention also relates to a method for producing a kit for detecting the particulate substance by immunochromatography. The production method of the present invention comprises steps of:

providing a test strip comprising a membrane on which first specific binding substance for the first substance to be bound is immobilized; and providing, in order to block the membrane, a blocking composition comprising a polymer-based blocking agent having, in its side chain, a substituent represented by the following formula:

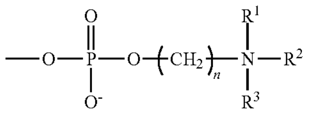

(wherein $R^1$, $R^2$, and $R^3$ are each independently a hydrogen atom, a $C_{1-6}$ alkyl group, or a $C_{1-6}$ hydroxyalkyl group; and n is an integer of 1 to 4), preferably a phosphorylcholine group, and having a weight average molecular weight (Mw) of about $1\times10^3$ to about $1\times10^7$, preferably about $5\times10^3$ to about $1\times10^6$. In an embodiment, the polymer-based blocking agent may further have at least one additional side chain selected from the group consisting of a cationic side chain, an anionic side chain, a hydrogen-bonding side chain, and a hydrophobic side chain.

In an embodiment, the production method of the present invention further comprises a step of blocking the membrane with the blocking composition. Further, in an embodiment, the production method of the present invention further comprises a step of preparing a second specific binding substance for the second substance to be bound, the second specific binding substance binding to a labeling substance; and a step of blocking the second specific binding substance with the blocking composition.

The detection method or production method of the present invention may further comprise any step generally used in the art as long as the purpose thereof is not impaired. For example, the detection method or suppression method of the present invention may comprise a step of isolating or purifying the particulate substance.

Further, in another embodiment, the present invention also relates to a kit for detecting the particulate substance by immunochromatography. The kit of the present invention comprises:

a test strip comprising a membrane on which a first specific binding substance for the first substance to be bound is immobilized; and a second specific binding substance for the second substance to be bound, the second specific binding substance binding to a labeling substance;

wherein in order to block the membrane, the kit further comprises a blocking composition comprising a polymer-based blocking agent having, in its side chain, a substituent represented by the following formula:

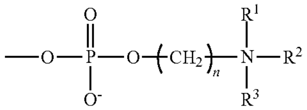

(wherein $R^1$, $R^2$, and $R^3$ are each independently a hydrogen atom, a $C_{1-6}$ alkyl group, or a $C_{1-6}$ hydroxyalkyl group; and n is an integer of 1 to 4), preferably a phosphorylcholine group, and having a weight average molecular weight (Mw) of about $1\times10^3$ to about $1\times10^7$, preferably about $5\times10^3$ to about $1\times10^6$; or the membrane is blocked with the blocking composition. In art embodiment, the polymer-based blocking agent may further have at least one additional side chain selected from the group consisting of a cationic side chain, an anionic side chain, a hydrogen-bonding side chain, and a hydrophobic side chain.

The kit of the present invention may further contain any component generally used in the art as long as the purpose thereof is not impaired. For example, the kit of the present invention may contain a buffer solution or an instruction manual.

The present invention is specifically described below with reference to Examples; however, the scope of the present invention is not limited to these Examples.

EXAMPLES

[Test Example 1]

1. Preparation of Exosome Solution

Using 10% FBS (name: Fetal Bovine Serum, manufacturer: Life Technologies), 1% PSA (name: Penicillin-Streptomycin-Amphotericin B Suspension (×100) (Antibiotic-Antimycotic Solution), manufacturer: FUJIFILM Wako Pure Chemical Corporation), and 20 ml of 2 mM Glutamax (manufacturer: Life Technologies)-containing RPMI 1640 medium, breast cancer cell strain MCF7 was cultured in a 150-mm dish to 80% of the bottom area of the dish. After the medium was removed, the cells were washed twice with 20 mL of phosphate buffered saline (PBS), and 20 mL of 2 mM Glutamax-containing Advanced RPMI 1640 Medium (manufacturer: Life Technologies) was added, followed by incubation for 48 hours. The cell culture supernatant (200 mL) for 10 150-mm dishes was centrifuged at 2,000×g at 4° C. for 10 minutes, the supernatant was centrifuged at 10,000×g at 4° C. for 30 minutes, and the final supernatant was filtered through a filter with a pore size of 0.22 μm. The filtrate was centrifuged at 175,000×g at 4° C. for 95 minutes, and the supernatant was removed to obtain a precipitated fraction. The precipitated fraction was dispersed in 13 mL of 1×PBS and centrifuged at 210,000×g at 4° C. for 95 minutes. After removal of the supernatant, the precipitate was redispersed in 0.2 mL of PBS to prepare an exosome solution. The particle number concentration of exosomes in the solution was measured by the NanoSight nanoparticle analysis system (produced by Malvern Panalytical). The solution was diluted with a diluent (10 mM PBS, 1% BSA, 0.05% Tween 20) as appropriate and used for subsequent tests.

2. Immunochromatographic Test

In the center portion of immunochromatographic test paper (produced by ForDx, Inc.) comprising a strip-shaped nitrocellulose membrane with a water absorption pad attached to one end thereof, mouse anti-CD9 antibody (product number: HBM-CD9-100, manufacturer: Hansa Bio Med Life Sciences) was immobilized by a conventional method. The membrane was blocked with phosphate buffered saline (PBS) containing each of the blocking agents shown in Table 1 below. Further, the mouse anti-CD9 antibody was labeled with HRP using Ab-10 Rapid Peroxidase Labeling Kit (LK33, produced by Dojindo Laboratories).

TABLE 1

| Blocking agent used | |
|---|---|
| Test group | Type of blocking agent |
| 1 | 1.5% BSA |
| 2 | 0.25 LIPIDURE ®-BL802 |
| 3 | 0.25 LIPIDURE ®-BL1002 |
| 4 | 1.5% BSA and 0.25% LIPIDURE ®-BL802 |
| 5 | 1.5% BSA and 0.25% LIPIDURE ®-BL1002 |

(LIPIDURE®-BL802 and LIPIDURE®-BL1002 are polymer-based blocking agents having a phosphorylcholine group in their side chain (produced by NOF Corporation), and their weight average molecular weight measured by GPC is $3.1\times10^4$ and $5.3\times10^4$, respectively.)

The water absorption pad-free end of the immunochromatographic test paper, on which the capture antibody was immobilized, was immersed in a test liquid (+) containing $2\times10^7$ exosomes or an exosome-free reference liquid (−), and they were developed. Next, a developing liquid containing mouse anti-CD9 antibody labeled with HRP was developed. Then, ImmunoStar® LD (product number: 290-59904, manufacturer: FUJIFILM Wako Pure Chemical Corporation) containing a luminol derivative was used to cause luminescence, and images were captured by Image Quant LAS 4000 with an exposure time of 80 seconds. The total luminance around the area where the capture antibody was immobilized (black (dark) image when luminescence occurred) and the total luminance of the same area where luminescence did not occur (white (bright) image) were measured by ImageJ, and their difference (luminance difference) was determined. Further, the S/N ratio was determined from a comparison between the test liquid and the reference liquid.

Figure 2:
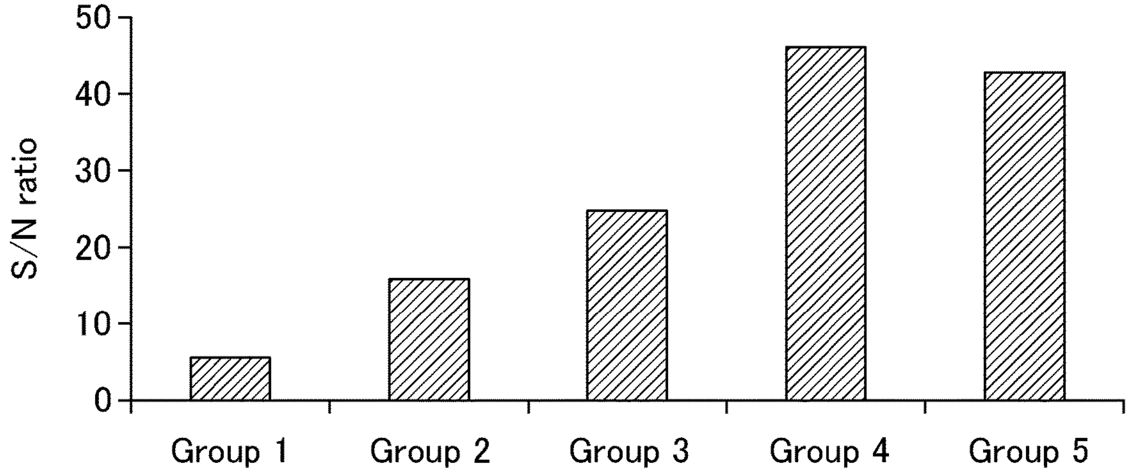
FIG. 2 shows a graph of the S/N ratio when exosomes were detected by immunochromatography.

FIG. 1 shows photographs of membranes after luminescence, and FIG. 2 shows a graph of the S/N ratio. When bovine serum albumin (BSA) was used as a blocking agent, non-specific signals in the background were strongly observed, and the S/N ratio was reduced; however, when LIPIDURE®-BL802 or LIPIDURE®-BL1002 was used, the generation of non-specific signals in the background was suppressed, and a high S/N ratio could be achieved. In addition, when LIPIDURE®-BL802 or LIPIDURE®-BL1002 was used in combination with BSA, the S/N ratio could be further increased.

[Test Example 2]

Exosomes were detected over time by immunochromatographv in the same manner as in Test Example 1, except that a test liquid containing $1\times10^7$ exosomes was used, and membranes were blocked with 1.5% BSA or PBS containing 0.25% LIPIDURE®-BL802. The detection intensity was determined by subtracting the background intensity from the total luminance difference (background intensity) of the background part and the total luminance difference of the capture antibody-immobilized part.

Figure 3:
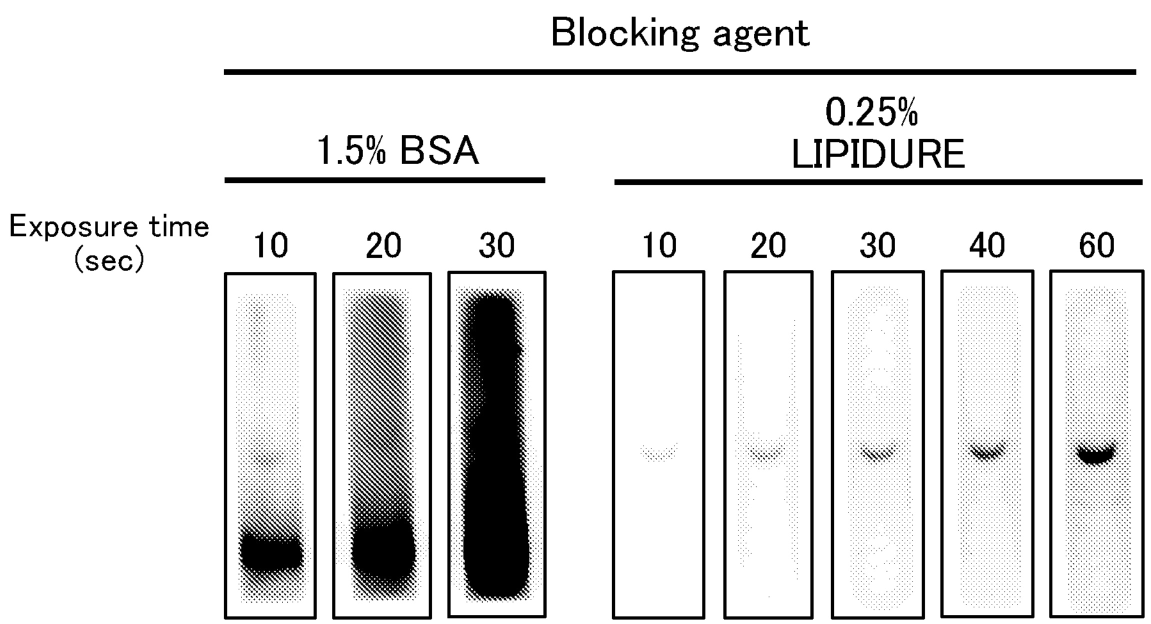
FIG. 3 shows photographs of membranes after luminescence when exosomes were detected over time by immunochromatography.
Figure 4:
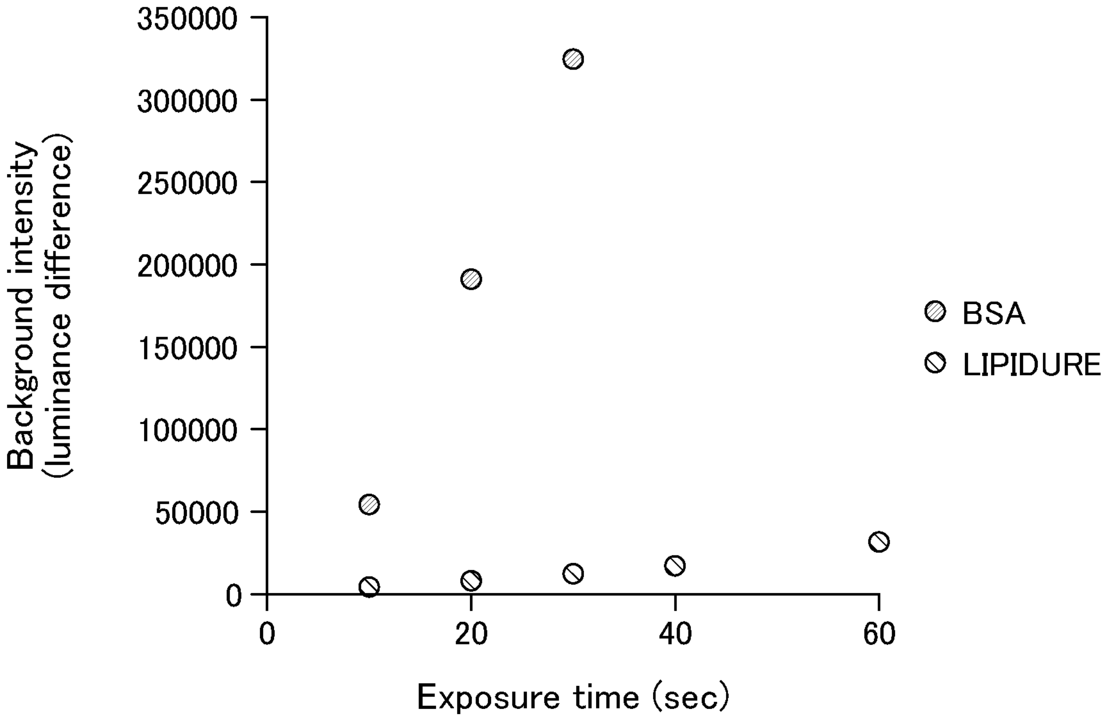
FIG. 4 shows a graph of background intensity when exosomes were detected over time by immunochromatography.
Figure 5:
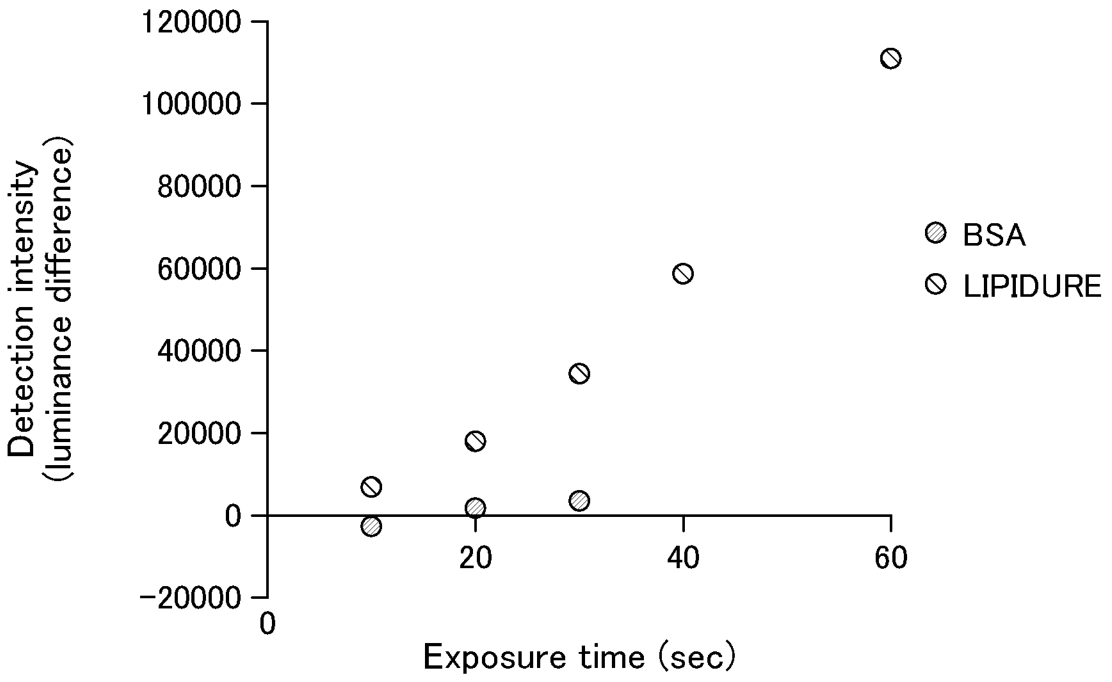
FIG. 5 shows a graph of detection intensity when exosomes were detected over time by immunochromatography.

FIG. 3 shows photographs of the membranes after luminescence, and FIGS. 4 and 5 show graphs of background intensity and detection intensity, respectively. When BSA was used as a blocking agent, non-specific signals in the background were too high (FIGS. 3 and 4). Therefore, the color of the entire membrane was saturated after 30 seconds of exposure, and the measurement device stopped automatically after 40 seconds of exposure. On the other hand, when LIPIDURE®-BL802 was used as a blocking agent, the generation of non-specific signals in the background was suppressed (FIGS. 3 and 4). Therefore, measurement with a longer exposure time was possible, and exosomes could be detected with high intensity (FIG. 5).

[Test Example 3]

Exosomes were detected over time by immunochromatography in the same manner as in Test Example 2, except that membranes were blocked with PBS containing 0.25% LIPIDURE®-BL802 or PBS containing 1.5% BSA and 0.25% LIPIDURE®-BL802. Then, the detection intensity was determined.

Figure 6:
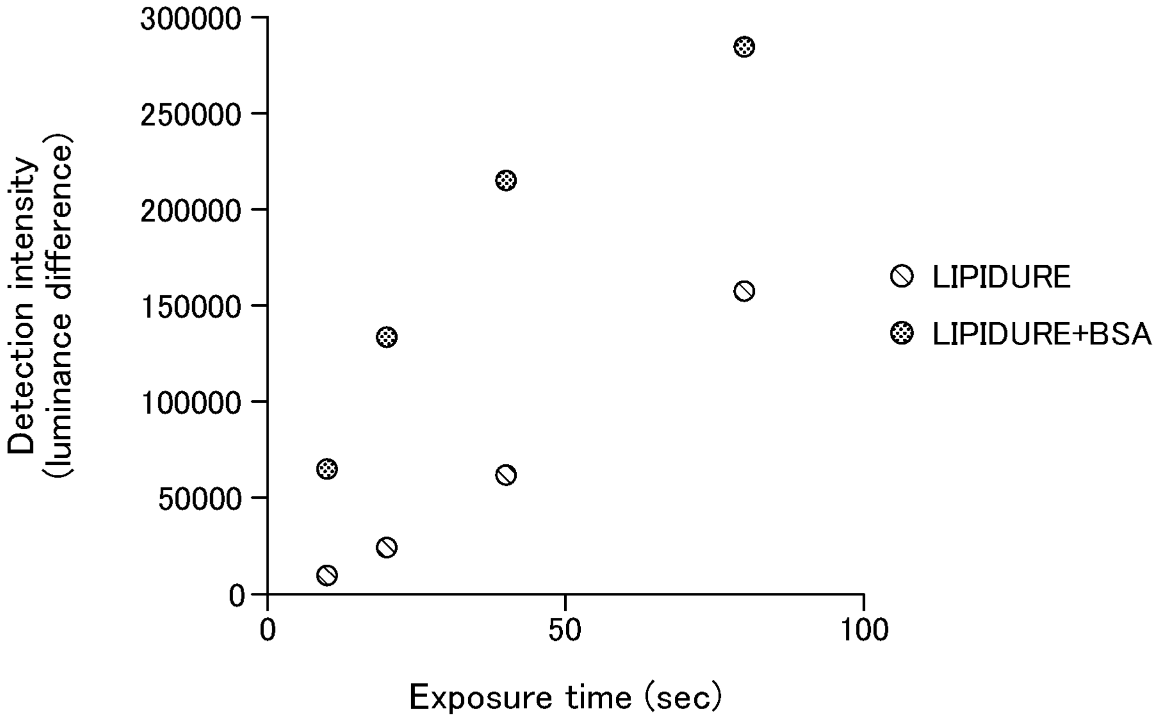
FIG. 6 shows a graph of detection intensity when exosomes were detected over time by immunochromatography.

FIG. 6 show a graph of detection intensity. Exosomes could be detected with sufficient intensity when using LIPIDURE®-BL802 alone; however, when using this in combination with BSA, the generation of non-specific signals in the background was further suppressed, and exosomes could be detected with higher intensity.

[Test Example 4]

Exosomes were detected over time by immunochromatography in the same manner as in Test Example 2, except that the number of exosomes used was set to 0, $1.1\times10^6$, $3.3\times10^6$, $10\times10^6$, or $30\times10^6$, and membranes were blocked with PBS containing 1.5% BSA or PBS containing 1.5% BSA and 0.25% LIPIDURE®-BL802. Then, the detection intensity was determined.

Figure 7:
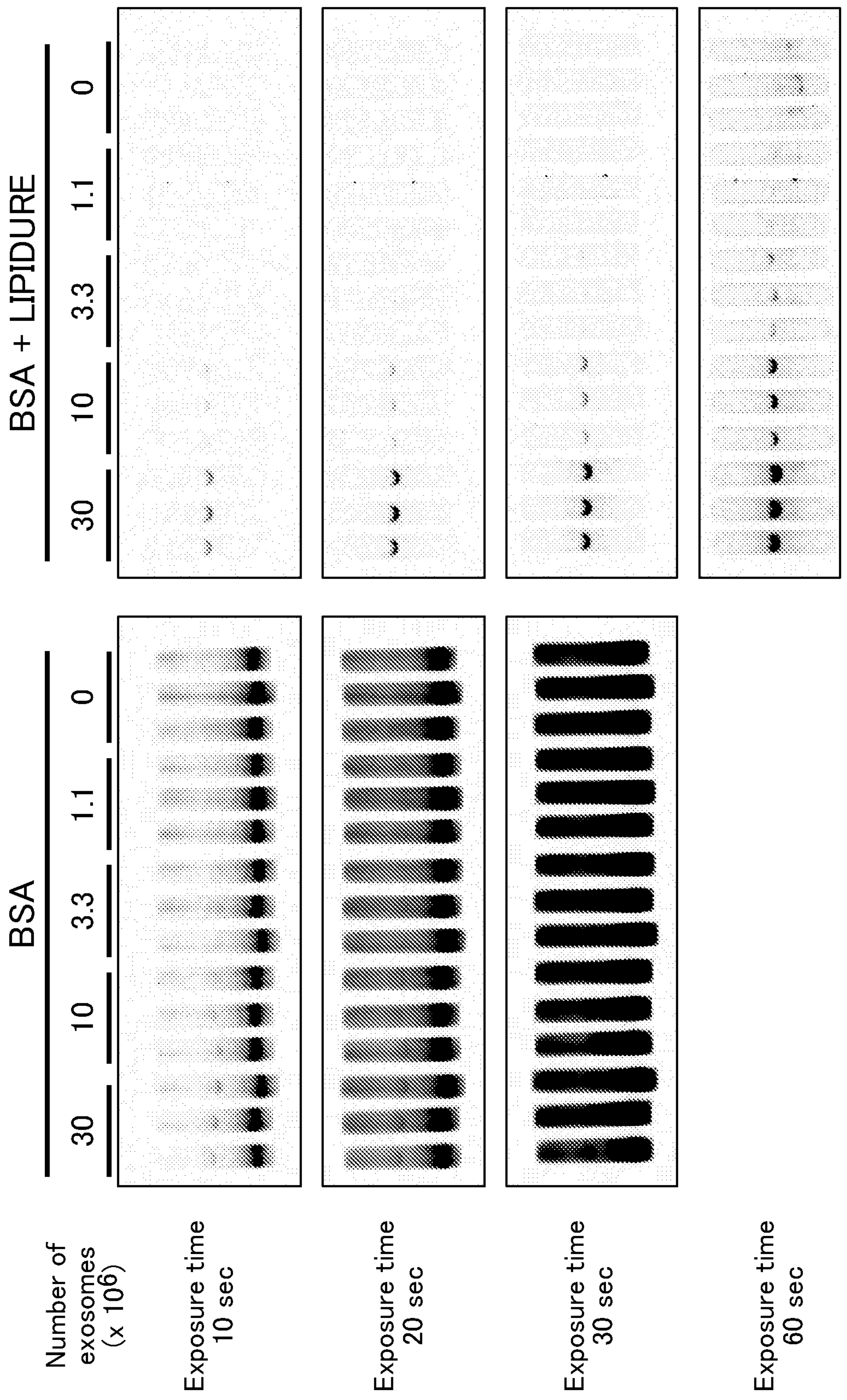
FIG. 7 shows photographs of membranes after luminescence when exosomes were detected over time by immunochromatography.
Figure 8:
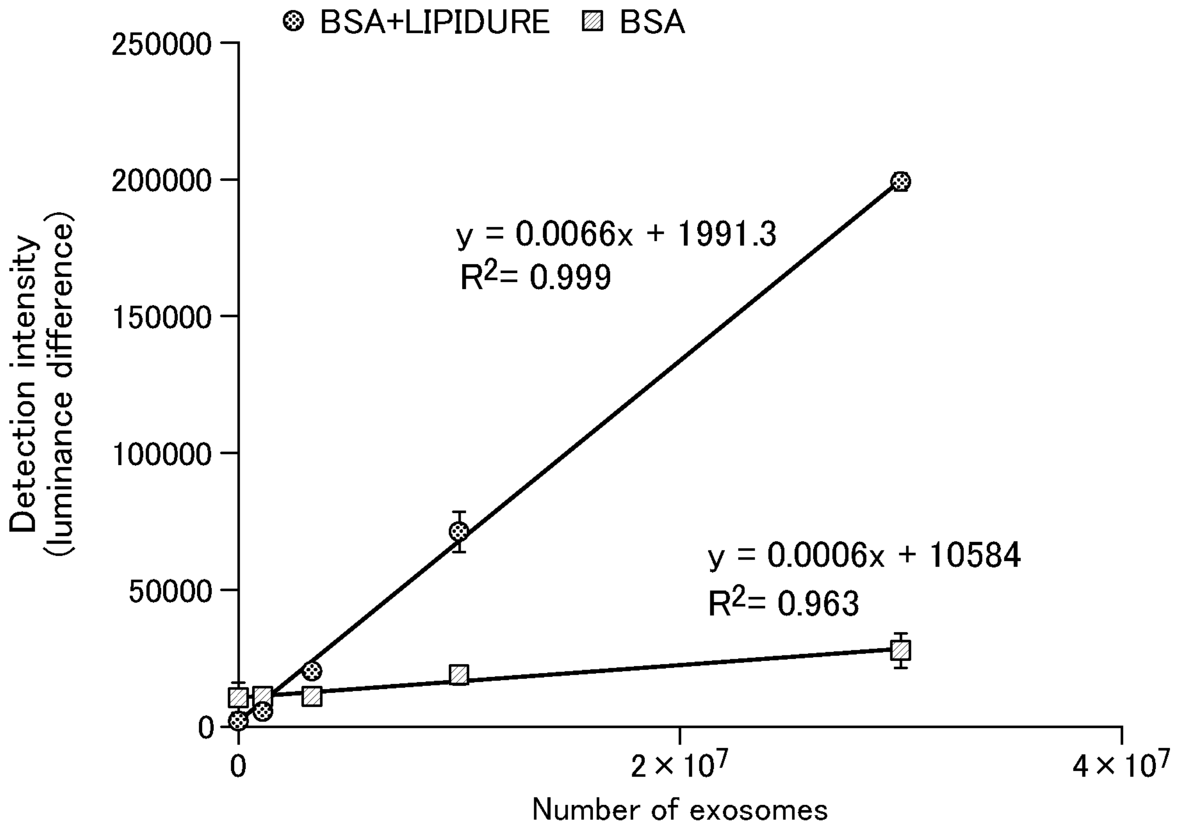
FIG. 8 shows a graph of detection intensity when exosomes were detected over time by immunochromatography.

FIG. 7 shows photographs of the membranes after luminescence, and FIG. 8 shows a graph of detection intensity (exposure time for BSA: 10 seconds; exposure time for BSA and LIPIDURE®-BL802: 60 seconds). When BSA alone was used as a blocking agent, non-specific signals in the background were increased. Therefore, only measurement with a short exposure time was possible, and a small amount of exosomes could not be detected. On the other hand, when LIPIDURE®-BL802 was added as a blocking agent, the generation of non-specific signals in the background was suppressed, and measurement with a long exposure time was possible. Therefore, a small amount of exosomes could be detected well. More specifically, when the detection limit (=3.3×s/a) was determined from the standard deviation (s) of the blank (group of 0 exosomes) and the slope (a) of the approximate straight line (calibration curve), it was about $3\times10^7$ when BSA alone was used as a blocking agent, whereas it was about $3\times10^5$ when LIPIDURE®-BL802 was used as a blocking agent.

[Test Example 5]

Using a breast cancer cell strain, MDA-MB-231 lymph node metastatic cells (MM231-LN cells), an exosome solution was prepared in the same manner as in the case of using MCF7 cells. Then, exosomes were detected by immunochromatography in the same manner as in Test Example 2, except that an exosome-free diluted solution or a test liquid containing $1\times10^{10}$ exosomes derived from MM231-LN cells was used, rabbit anti-LAM5 antibody (product number: ab14509, manufacturer: Abcam) was used as the antibody, membranes were blocked with PBS containing 0.25% LIPIDURE®-BL802, a developing liquid containing rabbit anti-LAM5 antibody labeled with HRP was used for detection, and a group obtained by adding LIPIDURE®-BL802 at a final concentration of 0.05% to the developing liquid containing the HRP-labeled antibody, and a group without the addition were prepared.

Figure 9:
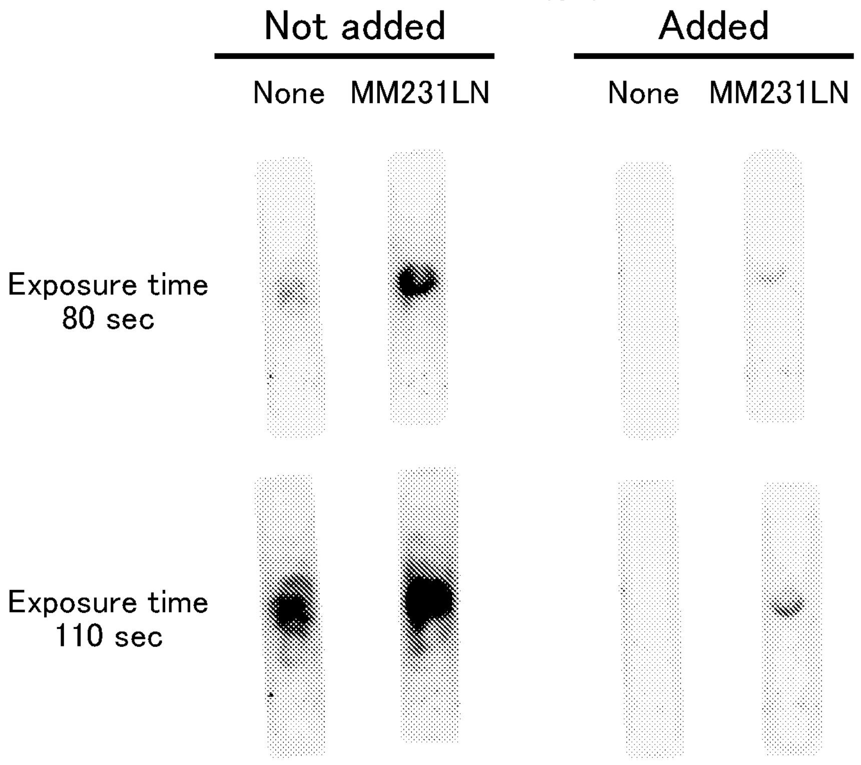
FIG. 9 shows photographs of membranes after luminescence when exosomes were labeled in the presence of LIPIDURE®.

FIG. 9 shows photographs of the membranes after luminescence. In order to detect a small amount of LAM5 present in the exosome solution derived from MM231-LN, it was necessary to increase the exposure time. When the developing liquid did not contain LIPIDURE®-BL802, non-specific luminescence was detected at the capture antibody-immobilized site even in the exosome-free test group; however, when LIPIDURE®-BL802 was added to the developing liquid, non-specific luminescence at the capture antibody-immobilized site was suppressed. Therefore, the test results were optimized, and the specific luminescence of MM231-LN was well detected.

[Test Example 6]

In the center Portion of immunochromatographic test paper (produced by ForDx, Inc.) comprising a strip-shaped nitrocellulose membrane with a water absorption pad attached to one end thereof, mouse anti-CD9 antibody (product number: HBM-CD9, manufacturer: Hansa Bio Med Life Sciences) was immobilized by a conventional method. The membrane was blocked with PBS containing 3% BSA or PBS containing 3% BSA and 0.5% LIPIDURE®-BL802. Then, the water absorption pad-free end of the immunochromatographic test paper, on which the capture antibody was immobilized, was immersed in a test liquid containing $5\times10^8$ exosomes or an exosome-free reference liquid, and they were developed. Next, a developing liquid containing mouse anti-CD9 antibody labeled with spherical gold nanoparticles (produced by BBI Solutions) by a conventional method was developed. Then, the colored membrane was visually observed.

Figure 10:
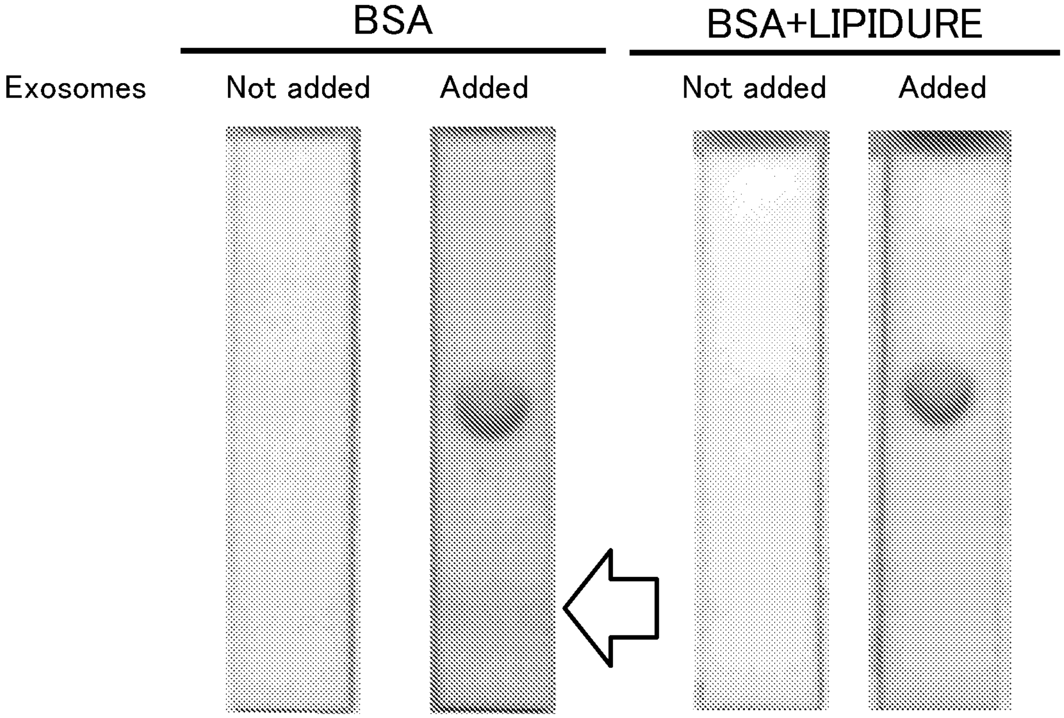
FIG. 10 shows photographs of membranes in the case of detection using spherical gold nanoparticie-labeled mouse anti-CD9 antibody.

FIG. 10 shows photographs of the membranes after the developing liquid was used. When BSA alone was used as a blocking agent, non-specific coloring of the background was observed below the capture antibody site (arrowed part in FIG. 10). When BSA was used in combination with LIPIDURE®-BL802, such non-specific coloring was not observed.

[Reference Example 1]

In the center portion of immunochromatographic test paper (produced by ForDx, Inc.) comprising a strip-shaped nitrocellulose membrane with a water absorption pad attached to one end thereof, mouse anti-human chorionic gonadotropin (hCG) antibody was immobilized by a conventional method. The membrane was blocked with PBS containing 1.5% BSA or PBS containing 0.25% LIPIDURE®BL802. Then, the water absorption pad-free end of the immunochromatographic test paper, on which the capture antibody was immobilized, was immersed in a test liquid containing 0.1 mIU hCG, and it was developed. Next, a developing liquid containing mouse anti-hCG antibody labeled with HRP by a conventional method was developed. Then, immunoStar® LD was used to cause luminescence, which was measured over time by Image Quant LAS 4000.

Figure 11:
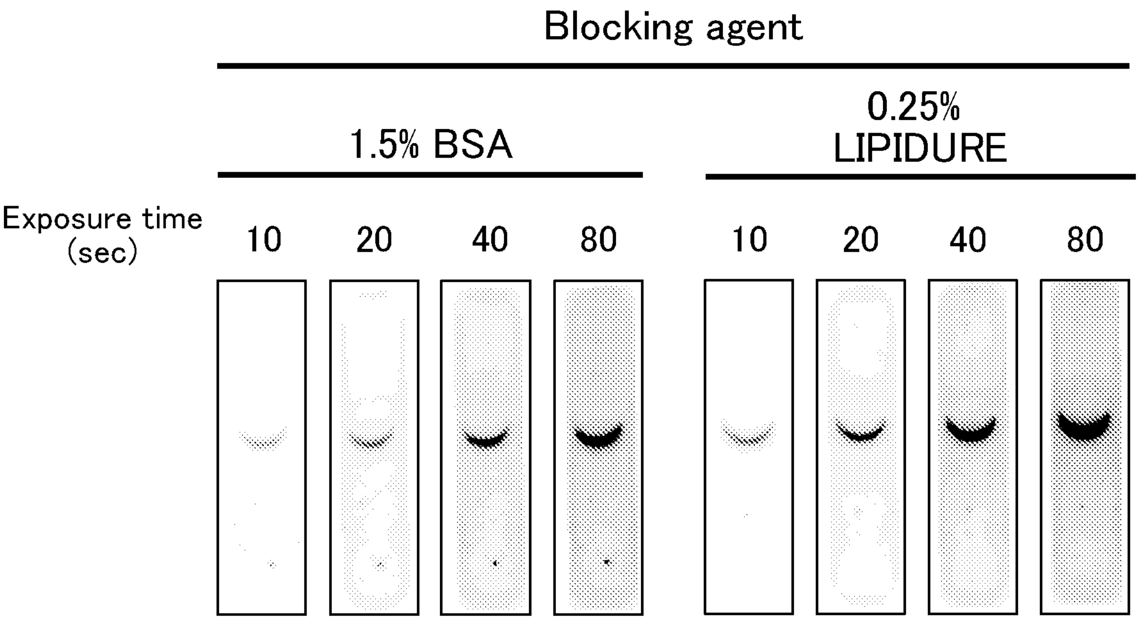
FIG. 11 shows photographs of membranes after luminescence when human chorionic gonadotropin (hCG) was used a subject to be detected by immunochromatography.

FIG. 11 shows photographs of the membranes after luminescence. Unlike the case where exosomes were used the detection target, when hCG was used as the detection target, non-specific signals in the background were not so increased even when using BSA as a blocking agent. Therefore, even when using LIPIDURE® as a blocking agent, the degree of improvement in background intensity or detection intensity was not so significant.

[Reference Example 2]

Mouse anti-CD9 antibody was immobilized on a 96-well microplate by a conventional method. Each well was blocked with 1.5% BSA or PBS containing 0.25% LIPIDURE®-BL802. Then, exosome-free PBS or PBS containing $1\times10^8$ exosomes was added to each well, and the captured exosomes were labeled with BRP-labeled mouse anti-CD9 antibody. A mixed solution of luminol and hydrogen peroxide was added to each well to cause luminescence, which was measured over time by Image Quant LAS 4000.

Figure 12:
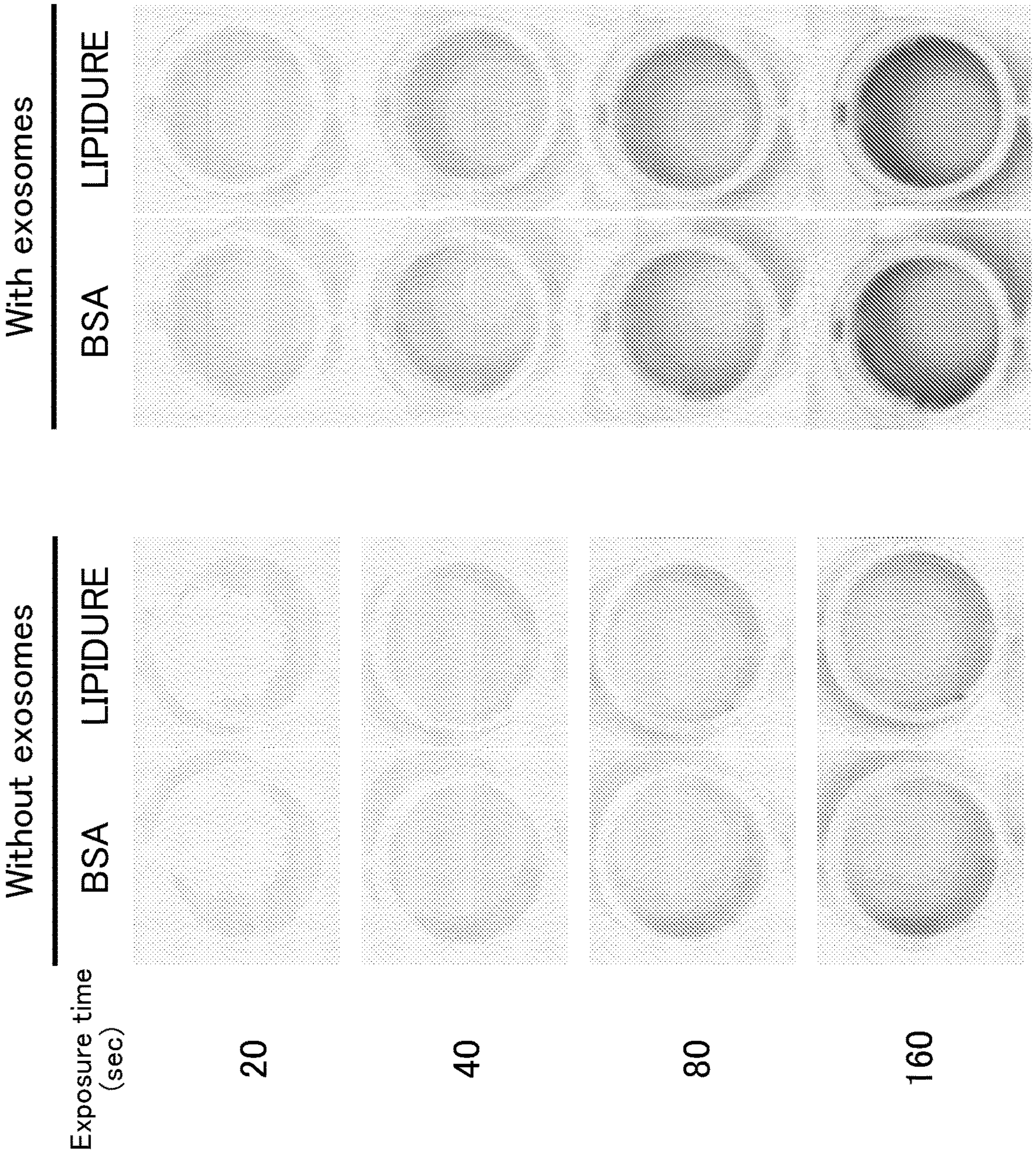
FIG. 12 shows photographs of wells after luminescence when an attempt was made to detect exosomes by the ELISA method.

FIG. 12 shows photographs of the wells after luminescence. Unlike the case of detection by immunochromatography, in the case of detection by the ELISA method using a 96-well microplate, no significant difference was observed when using BSA or LIPIDURE® as a blocking agent.

In view of the above, it was found that the generation of non-specific signals in the background can be suppressed by blocking a membrane of a test strip which is used for immunochromatography with a blocking composition comprising a polymer-based blocking agent having a specific substituent, such as LIPIDURE®. Therefore, particulate substances can be detected with high sensitivity by immunochromatography.

What is claimed is:

1. A method for detecting a particulate substance contained in various body fluids, including breast milk, saliva, and tears, as well as blood and urine; preservative solutions for tissue sections; or cell culture supernatants by immunochromatography, the particulate substance comprising, on its surface, a plurality of substances to be bound including a first substance to be bound and a second substance to be bound that may be the same or different from each other, the method comprising steps of:

providing a test strip comprising a membrane on which a first specific binding substance for the first substance to be bound is immobilized, wherein the membrane is blocked with a blocking composition comprising a polymer-based blocking agent having, in its side chain, a substituent represented by the following formula:

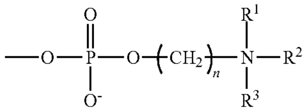

(wherein $R^1$, $R^2$, and $R^2$ are each independently a hydrogen atom, a $C_{1-6}$ alkyl group, or a $C_{1-6}$ hydroxyalkyl group; and n is an integer of 1 to 4), and having a weight average molecular weight (Mw) of $1\times10^3$ to $1\times10^7$;

providing a second specific binding substance for the second substance to be bound, the second specific binding substance binding to a labeling substance;

contacting a sample containing the particulate substance with the first specific binding substance to capture the particulate substance on the membrane;

contacting the particulate substance with the second specific binding substance to label the particulate substance;

detecting the labeled particulate substance captured on the membrane.

2. The method according to claim 1, wherein the particulate substance comprises extracellular vesicles.

3. The method according to claim 2, wherein the extracellular vesicles are exosomes.

4. The method according to claim 1, wherein the detecting step is performed by measuring chemiluminescence or fluorescence.

5. The method according to claim 1, wherein the labeling step is performed in the presence of the polymer-based blocking agent.

6. The method according to claim 1, wherein the polymer-based blocking agent is LIPIDURE®.

7. The method according to claim 1, wherein the blocking composition further comprises an additional blocking agent.

8. A method for producing a kit for detecting a particulate substance contained in various body fluids, including breast milk, saliva, and tears, as well as blood and urine; preservative solutions for tissue sections; or cell culture supernatants by immunochromatography, the particulate substance comprising, on its surface, a plurality of substances to be bound including a first substance to be bound and a second substance to be bound that may be the same or different from each other, the method comprising steps of:

providing a test strip comprising a membrane on which a first specific binding substance for the first substance to be bound is immobilized;

providing, in order to block the membrane, a blocking composition comprising a polymer-based blocking agent having, in its side chain, a substituent represented by the following formula:

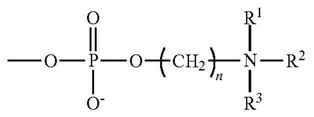

(wherein $R^1$, $R^2$, and $R^2$ are each independently a hydrogen atom, a $C_{1-6}$ alkyl group, or a $C_{1-6}$ hydroxyalkyl group; and n is an integer of 1 to 4), and having a weight average molecular weight (Mw) of $1\times10^3$ to $1\times10^7$;

blocking the membrane with the blocking composition.

9. The production method according to claim 8, further comprising steps of:

providing a second specific binding substance for the second substance to be bound, the second specific binding substance binding to a labeling substance; and blocking the second specific binding substance with the blocking composition.

10. A kit for detecting a particulate substance contained in various body fluids, including breast milk, saliva, and tears, as well as blood and urine; preservative solutions for tissue sections; or cell culture supernatants by immunochromatography, the particulate substance comprising, on its surface, a plurality of substances to be bound including a first substance to be bound and a second substance to be bound that may be the same or different from each other, the kit comprising:

a test strip comprising a membrane on which a first specific binding substance for the first substance to be bound is immobilized, wherein the membrane is blocked with a blocking composition comprising a polymer-based blocking agent having, in its side chain, a substituent represented by the following formula:

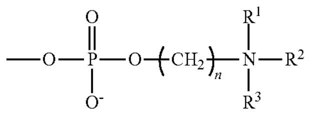

(wherein $R^1$, $R^2$, and $R^2$ are each independently a hydrogen atom, a $C_{1-6}$ alkyl group, or a $C_{1-6}$ hydroxyalkyl group; and n is an integer of 1 to 4), and having a weight average molecular weight (Mw) of $1\times10^3$ to $1\times10^7$;

a second specific binding substance for the second substance to be bound, the second specific binding substance binding to a labeling substance.

* * * * *